United States Patent [19]

Ritzl

[11] Patent Number: 4,609,289

[45] Date of Patent: Sep. 2, 1986

[54] SPECTROMETER

[76] Inventor: Hermann Ritzl, Hauptstrasse 60, 8031 Seefeld 2, Fed. Rep. of Germany

[21] Appl. No.: 623,751

[22] Filed: Jun. 22, 1984

[30] Foreign Application Priority Data

Jul. 15, 1983 [DE] Fed. Rep. of Germany ....... 3325659

[51] Int. Cl.$^4$ .............................................. G01J 3/02
[52] U.S. Cl. ..................................... 356/326; 356/317
[58] Field of Search ............... 356/319, 326, 328, 121, 356/218, 225, 226, 317, 318; 350/169, 171, 172

[56] References Cited

U.S. PATENT DOCUMENTS

| 3,554,647 | 1/1971 | Paine ................................... | 356/302 |
| 4,070,112 | 1/1978 | Tsunazawa et al. ................. | 356/319 |
| 4,260,255 | 4/1981 | Wachs et al. .......................... | 356/73 |
| 4,373,813 | 2/1983 | Reid et al. ............................. | 356/326 |

Primary Examiner—F. L. Evans
Attorney, Agent, or Firm—Jones, Tullar & Cooper

[57] ABSTRACT

A spectrometer which comprises a light source for exciting a sample, and a monochromator whose intensity values, as detected at the output gap, are subjected to further processing in a computer, in conjunction with the associated wavelength values, for the purposes of achieving a large measuring range and a high degree of measuring accuracy is provided with two secondary electron multipliers and a beam splitter which supplies the second secondary electron multiplier with only a small fraction of the radiation issuing from the monochromator. An electronic switch transmits to the computer, by way of an A-D converter, the output of that secondary electron multiplier whose output signal is within the analysable range of levels. The computer causes the monochromator to pass through the measuring range a plurality of times, and individually stores the measurement values which are then processed to form mean values.

4 Claims, 1 Drawing Figure

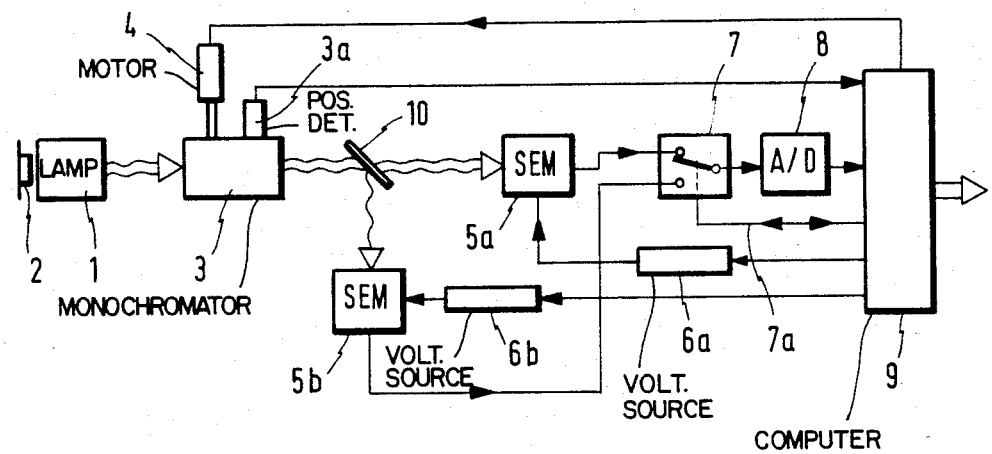

SPECTROMETER

BACKGROUND OF THE INVENTION

The invention relates to a spectrometer comprising a light source for exciting a sample, a motor-adjustable monochromator, a secondary electron multiplier connected to an adjustable operating voltage source, with, on its output side, an A-D converter, and a computer which stores the output signals thereof and the associated wavelength and which controls the position of the monochromator and which regulates the operating voltage source of the secondary electron multiplier in accordance with a stored relationship between the operating voltage and the spectral sensitivity of the spectrometer, with the wavelength of the radiation as adjusted at the monochromator.

A spectrometer of that kind is disclosed in U.S Pat. No. 4,373,813 and can be used for example to determine the percentage content of various chemical elements in the sample, as the output signal level of the secondary electron multiplier, when the monochromator is set to a spectral line which is characteristic in respect of a given chemical element, is a direct measurement of the amount of the element in question, in the sample.

As the width of a spectral line is only about one three hundred thousandths of the spectrum between about 2000 and 6000 Å, such spectrometers require monochromators with a high degree of resolution in order to be able to separate closely adjacent lines from each other and provide a clear association with a given wavelength. Suitable monochromators with a degree of resolution of up to 1.6 millions of points (with respect to a rotary movement of 360°) are available on the market. It is also known from U.S. Pat. No. 3,868,499 for the monochromator of a spectrometer to be caused to pass through the spectrum in a computer-controlled mode, for which purpose the monochromator is provided with a stepping motor and a position detector.

For certain uses of spectrometry, for example for spectral analysis to determine the composition of a metallurgical sample, very wide measuring ranges of for example 0.001% to 100% content are required, with at the same time a high degree of measuring accuracy of 0.5 parts per thousand (with respect to the aboslute value). The spectrometer of the general kind set forth in the opening part of this specification cannot cover such a measuring range and cannot achieve such a degree of accuracy as, having regard to the necessary noise signal ratio, with a given operating high tension (with respect to a given spectral range), the secondary electron multiplier produces a useful output signal at most over the range of three decimal powers, that is to say, it only covers a measuring range of from example 0.01% to 10%.

The invention is based on the problem of providing a spectrometer of the kind set forth in the opening part of this specification, which permits time-saving and fully automatic recording of the spectrum emitted by a sample, with an increased measuring range and an enhanced degree of measuring accuracy.

SUMMARY OF THE INVENTION

According to the invention, that problem is solved in that disposed in the ray path between the monochromator and the secondary electron multiplier is a beam splitter which feeds a small fraction of the radiation energy to a second secondary electron multiplier which is also connected to an operating voltage source which can be regulated by way of the computer, that the outputs of the two secondary electron multipliers are connected to the input of the A-D converter by way of a controllable electrical switch whose control input is connected to the computer, and that the computer causes the monochromator to pass through the spectrum to be investigated a plurality of times continuously in alternate directions, and, from the respectively stored individual values in respect of radiation intensity, after removal of the background noise, computes a mean value.

In that arrangement, by virtue of using two secondary electron multipliers, a wide measuring range of about six decimal powers is achieved, while the repeated movement through the spectrum being investigated and the subsequent operation of forming the mean value ensure the high degree of measuring accuracy. The latter may be further enhanced by a plurality of lines being measured, per element, and by taking account of the fact, when forming the mean value, that the individual measurement values must be in a Gaussian distribution. In that way it is possible in particular also to measure very small contents, that is to say, very weak lines which only very slightly rise above the background and therefore have a very small signal-to-noise ratio.

BRIEF DESCRIPTION OF DRAWINGS

The drawing shows in diagrammatically simplified form a block circuit diagram of an embodiment selected by way of example of an emission spectrometer according to the invention.

DESCRIPTION OF PREFERRED EMBODIMENT

A light source 1, for example a glow discharge lamp, excites a sample 2. The emitted radiation passes through a monochromator 3 which acts as a continuously tunable filter. For that purpose, a stepping motor 4 which is controlled by a computer 9 drives the movable gate or grid of the monochromator 3, the position of which is fed back to the computer 9 by way of a position detector 3a.

The radiation issuing from the monochromator impinges on a first secondary electron multiplier 5a. Disposed in the ray path is a beam splitter 10 which deflects for example one thousandth of the radiation towards a second secondary electron multiplier 5b, the axis of which is normal to the axis of the first secondary electron multiplier 5a. The beam splitter 10 may advantageously comprise a thin bare wire.

The secondary electron multipliers 5a and 5b are connected to separate high tension sources 6a and 6b. The operating voltage supplied by the high tension sources establishes the sensitivity range of the respective secondary electron multiplier. The high tension sources 6a and 6b respectively are therefore so adjusted that the secondary electron multiplier 5a produces for example an output signal of 0.01 to 10 V, corresponding to a content of 0.1 to 100%, and the secondary electron multiplier 5b produces an output signal of 0.1 to 10 V, corresponding to a content of 0.001% to 0.1%. As the secondary electron multipliers have a level of sensitivity which is dependent on the wavelength of the incident light, the operating voltages which are outputted by the high tension sources to the associated secondary electron multipliers can be controlled by way of the computer 9. For that purpose, the computer 9 stores the relationship between the wavelength and the associated sensitivity of the secondary electron multipliers.

The signal outputs of the secondary electron multipliers 5a and 5b are connected to two separate inputs of an electronic switch 7, the output of which is connected by way of an A-D converter 8 to the computer 9. The switch 7 in each case switches through the output of that secondary electron multiplier whose output signal is of the greater value, without exceeding the admissible maximum value of for example 10 V, on the other side of which begins the saturation or overload range. By way of the line 7a, the computer receives information about the instantaneous position of the switch 7, if the latter automatically decides which output of the secondary electron multipliers is switched through to the A-D converter. Another possibility is for that decision to be made by the computer 9 which then puts the switch 7 into the corresponding position, by way of the line 7a. It will be appreciated that other electronic constructions are also possible, in this area. In particular, separate A-D converters may be connected to the outputs of the secondary electron multipliers 5a and 5b, and are in turn both connected to the computer 9 which takes the decision as to which converter output signal is to be subjected to further processing.

The computer stores the measured intensity values, in conjunction with the associated wavelengths, more specifically upon repeatedly passing through the spectrum, in separate storage locations. At the same time, the value of the background, which belongs to the measured spectral lines, is stored. After termination of the measuring programme, the stored values are converted into mean values and they are then converted into percentage values which are then for example printed out.

I claim:

1. A spectrometer comprising a light source for exciting a sample, a motor-adjustable monochromator, a secondary electron multiplier connected to an adjustable operating voltage source, with, on its output side, an A-D converter, and a computer which stores the output signals thereof and the associated wavelength and which controls the position of the monochromator and which regulates the operating voltage source of the secondary electron multiplier in accordance with a stored relationship between the operating voltage and the spectral sensitivity of the spectrometer, with the wavelength of the radiation as adjusted at the monochromator, characterised in that disposed in the ray path between the monochromator (3) and the secondary electron multiplier (5a) is a beam splitter (10) which feeds a small fraction of the radiation energy to a second secondary electron multiplier (5b) which is also connected to an operating voltage source (6b) which can be regulated by way of the computer (9), that the outputs of the two secondary electron multipliers (5a, 5b) are connected to the input of the A-D converter (8) by way of a controllable electrical switch (7) whose control input is connected to the computer (9), and that the computer causes the monochromator (3) to pass through the spectrum to be investigated a plurality of times continuously in alternate directions, and, from the respectively stored individual values in respect of radiation intensity, after removal of the background noise, computes a mean value.

2. A spectrometer according to claim 1 characterised in that the beam splitter comprises a thin wire.

3. A spectrometer for determining the mean values of measurements from a monochromator over a wide range of such measurements, comprising:
   a light source for exciting a sample to emit radiation having a spectrum of wavelengths;
   an adjustable monochromator receiving said radiation and producing output radiation of selected wavelengths from said spectrum;
   means for adjusting said monochromator to scan said spectrum of wavelengths;
   first and second substantially identical electron multipliers, each said multiplier producing an electrical output corresponding to the intensity of radiation received from said monochromator;
   beam splitter means directing a small fraction of said output radiation to said first electron multiplier and directing the remainder of said output radiation to said second electron multiplier;
   first and second variable operating voltage sources connected to said first and second electron multipliers, respectively, the operating voltage applied to said electron multipliers establishing the sensitivity ranges of the respective electron multipliers;
   an analog-to-digital converter;
   switch means for selectively connecting the output of said first or said second electron multiplier to the input of said analog-to-digital converter;
   computer means controlling said means for adjusting said monochromator for repeatedly scanning said spectrum of wavelengths continuously in alternate directions, receiving and storing the output signals from said analog-to-digital converter for each wavelength of said spectrum, and from the respectively stored individual wavelength values of radiation intensity, computing a mean value, said computer means regulating said means for adjusting said monochromator and regulating said first and second variable operating voltage sources to obtain a predetermined spectral sensitivity for each selected spectral wavelength.

4. The spectrometer of claim 3, wherein the sensitivity of said first electron multiplier is adjustable by said computer means to produce an output signal having a specified voltage range upon receipt of input radiation representing 0.001 percent to 0.1 percent spectral content, and wherein the sensitivity of said second electron multiplier is adjustable by said computer to produce an output signal having the same voltage range as said first electron multiplier upon receipt of input radiation representing 0.1 to 100 percent spectral content.

* * * * *